United States Patent [19]

Huber et al.

[11] 4,318,855
[45] * Mar. 9, 1982

[54] PROCESS FOR THE PREPARATION OF ALPHA-HYDROXYCARBONYL COMPOUNDS

[75] Inventors: Ulrich Huber, Zurich; Hans-Jakob Wild, Meilen, both of Switzerland

[73] Assignee: Givaudan Corporation, Clifton, N.J.

[*] Notice: The portion of the term of this patent subsequent to Jan. 1, 1997, has been disclaimed.

[21] Appl. No.: 114,938

[22] Filed: Jan. 24, 1980

[30] Foreign Application Priority Data

Feb. 2, 1979 [CH]  Switzerland ........................... 1024/79
Dec. 14, 1979 [CH]  Switzerland ......................... 11104/79

[51] Int. Cl.$^3$ .................... C07D 307/32; C07C 49/597
[52] U.S. Cl. .................... 260/343.6; 260/464; 560/122; 562/504; 568/347; 568/379
[58] Field of Search ............................. 260/343.6, 464; 568/343, 379, 347

[56] References Cited

U.S. PATENT DOCUMENTS 4,181,666  1/1980  Huber et al. ..................... 260/347.8

OTHER PUBLICATIONS

Migrdichian Organic Synthesis vol. 1 p. 429.
Roberts et al. Basic Principles of Organic Chemistry pp. 438–442.
Reininger Chem. Ber. 106, 1309 (1973) plus English Abstract.
Selikson et al. J. Org. Chem. 40 267 (1975).
Hori, Chem. Abstract 58, 5508b.
March, Advanced Organic Chemistry, pp. 477–478.

*Primary Examiner*—John M. Ford
*Assistant Examiner*—Jane T. Fan
*Attorney, Agent, or Firm*—Robert F. Tavares; Thomas Cifelli, Jr.

[57] ABSTRACT

The instant invention provides a new and improved method of preparing α-hydroxycarbonyl compounds, particulary substituted cyclopent-2-en-2-ol-1-ones and substituted 3-hydroxy-2(5H)-furanones. The novel sequence involves a number of novel intermediates including substituted 2-cyanocyclopentanones, substituted 2-cyano-2-hydroxycyclopentanones, and 2-cyano-2-hydroxyvalero-γ-lactones.

30 Claims, No Drawings

PROCESS FOR THE PREPARATION OF ALPHA-HYDROXYCARBONYL COMPOUNDS

THE INVENTION

This invention concerns a novel process for preparing a number of α-hydroxycarbonyl compounds, particularly substituted cyclopent-2-ol-1-ones and substituted 3-hydroxy-2(5H)-furanones. The novel process involves a novel sequence of steps which require the preparation of a number of novel intermediates.

The novel process can be illustrated as follows:

SCHEME I

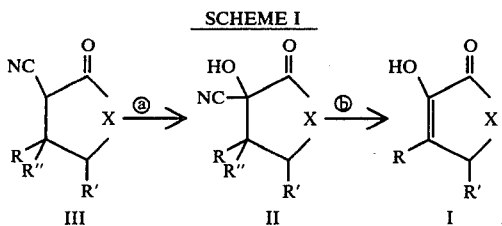

wherein:
R represents methyl or ethyl R' represents hydrogen, methyl or ethyl
X represents oxygen, >CH$_2$, >CHCH$_3$ or >CHCH$_2$CH$_3$
R" represents hydrogen when X is oxygen and represents —COOR'" or hydrogen when X is not oxygen.
R'" represents hydrogen or an alkyl group of one to six carbons.

Step ⓑ in Scheme I involves a cyanohydrin cleavage which can be carried out thermally or can be catalysed by acid or base. In those cases where R" is COOR'", the group R" is also removed either via a separate step or during the cyanohydrin cleavage step.

Step ⓐ involves the formation of the cyanohydrin II via the oxidation of the nitrile III.

The compounds of formula I are known flavoring substances and/or sugar degradation products.

The compounds of formula II are novel intermediates.

The compounds of formula III wherein X is not oxygen and R" is hydrogen are also novel.

DESCRIPTION OF THE PREFERRED EMBODIMENTS

The cyanohydrin cleavage (step ⓑ of Scheme I) can be carried out thermally, acid-catalysed or base-catalysed.

When the cyanohydrin cleavage is carried out thermally the compound of formula II is suitably heated to a temperature of ca 50° C. to 400° C., preferably of ca 80°-250° C.

When the cyanohydrin cleavage is acid catalysed, the compound of formula II is treated with an acid. The amount of acid is not critical. It is only essential that the pH of the reaction mixture be on the acid side, i.e. below 7. Suitably, the acid may be used in catalytic amounts (e.g. 1/1000-1/10 equivalents) or in larger amounts (e.g. molar amounts).

The nature of the acid is not critical. Examples of acids which can be used are inorganic acids (e.g. sulphuric acid, hydrochloric acid and sulphurous acid), organic acids (e.g. formic acid, acetic acid, citric acid and oxalic acid) or acid ion-exchangers (e.g. Amberlite IRC 50 etc).

In the base-catalysed cyanohydrin cleavage, a compound of formula II is treated with a base, the base being conveniently used in catalytic amounts (e.g. 1/1000-1/10 equivalents) or, however, also in larger (e.g. molar) amounts. It is only essential that the pH of the reaction mixture lies above 7.

The nature of the base is not critical. Examples of bases which can be used are inorganic bases such as alkali metal hydroxides (e.g. sodium hydroxide), alkaline earth metal hydroxides (e.g. calcium hydroxide and magnesium hydroxide), alkali metal carbonates (e.g. sodium carbonate and potassium carbonate), alkali metal bicarbonates (e.g. sodium bicarbonate), ammonia, other basic salts (e.g. sodium phosphate potassium hydrogen phosphate and borax), basic buffer systems (e.g. sodium bicarbonate/sodium carbonate, potassium hydrogen phosphate/potassium phosphate etc.), organic bases such as amines (e.g. triethylamine, pyridine, morpholine etc), salts of organic acids with strong bases (e.g. sodium acetate, formate, oxalate, citrate and lactate) or basic ion-exchangers (e.g. Amberlite IRA 400, Dowex 2 etc).

The cyanohydrin cleavage can be carried out in the gas phase or in the liquid phase. The presence of a solvent is not necessary, but is convenient.

The cyanohydrin cleavage is advantageously carried out at a temperature of 50°-200° C., preferably at ca 100° C.

The nature of the solvent is not critical. A polar solvent such as water, ammonia or an alcohol or an apolar solvent such as toluene, benzene, toluene, ether, petroleum ether etc can be used.

Preferred systems for carrying out the cyanohydrin cleavage are basic ion-exchangers in the OH⊖-form-/water, organic acids or their salts (e.g. acetic acid/water, sodium oxalate/water) or pyridine/toluene at a temperature of ca 100° C.

Where R" represents the group —COOR'", in which R'" represents hydrogen or a C$_{1-6}$-alkyl group, there is in principle first of all obtained after the cyanohydrin cleavage a compound of formula VI or formula VII hereinafter:

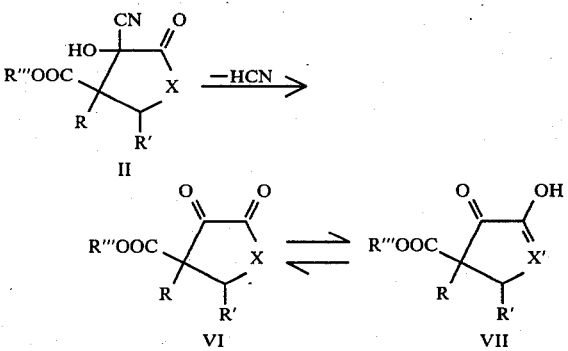

VI can also be present in the enol form VII (X' = >CH, >C—CH$_3$ or >C—C$_2$H$_5$).

This group —COOR'" can be readily cleaved by, for example, initially hydrolysing the ester group —COOR''' with an aqueous acid or base and then decarboxylating the (resulting) carboxylic acid or salt thereof (R'''=H, alkali metal or alkaline earth metal equivalent), the decarboxylation being carried out, for example, by thermal treatment (50°–200° C.).

The cleavage of the group —COOR''' can, however, also be carried out under the aforementioned conditions for the cyanohydrin cleavage, especially when the cyanohydrin cleavage is carried out under drastic conditions. The term "drastic conditions" is used to mean especially the following:

Acid treatment: pH $\leq$ 3, especially <2
Base treatment: pH $\geq$ 10, especially >12.

The compounds of formula II are novel and also form part of the present invention.

The compunds of formula II can advantageously be prepared by oxidizing a compound of the general formula

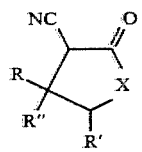

wherein R, R', R" and X have the significance given earlier.

Especially suitable oxidising agents are alkali metal caroates (e.g. $KHSO_5$). The preferred oxidising agent is "Caroat" (Trade Mark) ($KHSO_5$ containing $KHSO_4$ and $K_2SO_4$).

The caroate is conveniently used in an amount of 1–2.5 equivalents, especially 1.1–1.5 equivalents.

The oxidation is preferably carried out in a polar solvent such as water, an alcohol, acetone or acetonitrile or in a mixture of such solvents.

The pH of the medium in which the oxidation is carried out conveniently amounts to ca 3–11, such as can be generated by appropriate buffer systems of the carbonate, phosphate, citrate, borate, $NH_3/NH_4^\oplus$ or oxalate type in a manner known per se.

The oxidation can be carried out at a temperature of, for example, between $-10°$ C. and 60° C., preferably between 0° C. and 20° C.

Compounds of formula II in which R'" represents the group —COOR''' are preferred starting materials in the process provided by the present invention, especially since they can be readily prepared.

The compounds of formula III in which X is not an oxygen atom and R" represents a hydrogen atom are novel and also form part of the present invention.

The novel compounds of formula III, which can be represented by formula III'0 hereinafter, can be prepared especially from a dinitrile of formula IV according to the Thrope-Ziegler method (see, for example, The Merck Index, Encyclopedia of Chemicals and Drugs, 9th Ed., 1976, O.N.R. 87, Merck and Co., Rahway, N.J.) or by a Dieckmann cyclisation of a corresponding cyanoester of formula V (The Merck Index, vide supra, O.N.R. 23) as shown in the following Formula Scheme in which R and R' have the significance given earlier:

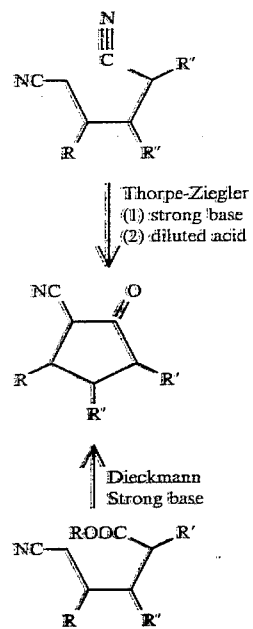

Further methods for the preparation of compounds of formula III' include known methods for the introduction of the cyano group into a corresponding cyclopentanone derivative such as a halogenation (e.g. a bromination) followed by a $CN^\ominus$-substitution [H. O. House, Modern Synthetic Reactions, Benjamin Publisher, Menlo Park (1972), 459 et seq; Organikum, organisch-chemisches Grundpraktikum, VEB deutscher Verlag der Wissenschaften 4th Ed., 1964, 283] or the action of a cyanogen halide on a corresponding cyclopentanone or its enamine derivative (see M. Kühne, J. Amer. Chem. Soc. 81, 5400, 1969) as shown in the following Formula Scheme in which R and $R^1$ have the significance given earlier:

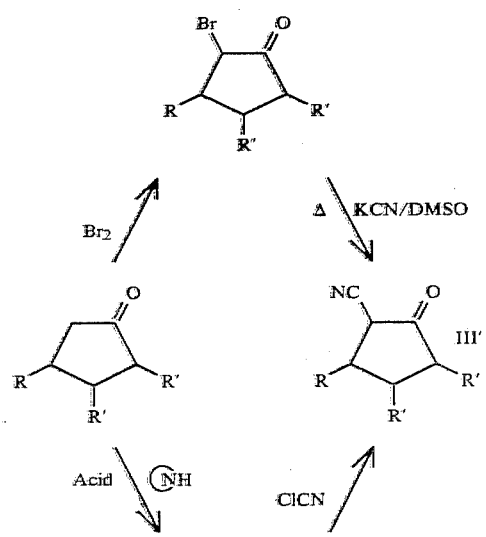

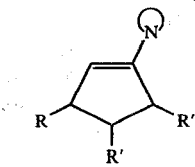

The α-hydroxycarbonyl compounds of formula I are generally known. They are flavouring substances and/or sugar degradation products.

The following Examples illustrate the present invention:

EXAMPLE 1

Manufacture of 3,4-dimethylcyclopent-2-en-2-olone (a) 67.1 g (1 mol) of crotonic acid nitrile and 76 g (0.65 mol) of ammonium perchlorate are placed in a reaction vessel and the mixture is treated while cooling to ca −70° C. with ca 260 g of anhydrous ammonia. A direct current voltage of 15 volts (4–5 amperes) is applied at −75° C. for 15 hours by means of a mercury cathode lying on the bottom of the vessel and a suspended graphite anode. The ammmonia is allowed to evaporate. The dark brown solution is taken up in 700 ml of ether and washed with 250 ml of water. The concentrated ether solution gives 31 g (46%) of 3,4-dimethyladiponitrile which is fractionally distilled at 107°–109° C./0.15 Torr.

(b) 5.6 g of potassium tert.butylate are refluxed for 60 minutes with 6.8 g of 3,4-dimethyladiponitrile in 50 ml of toluene. The cooled solution is washed with 50 ml of water and concentrated. There are obtained 6.4 g (94%) of 2-cyano-3,4-dimethyl-cyclopent-1-enylamine of melting point 92°–100° C.

IR (CHCl$_3$) 3500 and 3400 (NH), 2180 (CN), 1638 and 1596 (C=C).

MS: 136 (M+), 121 (100%), 94.

(c) 2 g of the product obtained according to paragraph (b) are stirred for 10 minutes with 50 ml of 2 N H$_2$SO$_4$ and subsequently extracted three times with 30 ml of ether each time. The dried and concentrated ether phases contain 1.8 g (89%) of 2-cyano-3,4-dimethylcyclopentanone of boiling point 75°–76° C./0.05 Torr.

IR: 2250 (CN), 1750 (strong, C=O).

MS: 137 (M+, 100%), 122, 108, 94, 69, 68.

(d) 2 g of the product obtained according to paragraph (c) are dissolved, together with 1.4 g of borax and 1.17 g of sodium hydroxide, in 20 ml of water and the solution is treated with 6.4 g of Caroat (Degussa). After 30 minutes, the mixture is filtered, acidified with sulphuric acid to pH 1 and extracted four times with 30 ml of methylene chloride each time. After concentration, there are obtained 1.57 g (71%) of an enantiomer mixture of 2-cyano-2-hydroxy-3,4-dimethylcyclopentanone; n$_D^{20}$=1.5490.

IR: 3150 (OH), 2250 (very weak, CN), 1710 (C=O).
MS: 139 (M+), 121, 112, 95, 83 (100%).

(e) 1 g of the product obtained according to paragraph (e) is refluxed with 0.8 g of sodium acetate for 6 hours in 15 ml of water and then extracted four times with ethyl acetate. By concentration of the ethyl acetate there is obtained 0.578 g (70%) of 3,4-dimethyl-cyclopent-2-en-2-ol-1-one in the form of brown crystals of melting point 69°–71° C. (from water).

NMR (CDCl$_3$): δ=5.8 ppm singlet, broad/1 pr (OH); 2.8–2.5 multiplet/2 pr (H-5); 2.2–1.8 multiplet/1 pr (H-4); 1.98 singlet/3 pr (CH$_3$ at C-3); 1.18 doublet (J=7 Hz)/3 pr (CH$_3$ at C-4).

The same product can be manufactured from the 2-cyano-2-hydroxy-3,4-dimethylcyclopentanone obtained as described in paragraph (d) by refluxing 2 g of the latter in 60 ml of saturated sodium bicarbonate solution for 4 hours and extracting the cooled solution four times with 30 ml of methylene chloride each time. From the concentrated organic phase there is obtained 0.98 g (60%) of pure (GC and TLC) crystalline product of melting point 66°–68° C. The recrystallisation is carried out from water.

EXAMPLE 2

Manufacture of 3-hydroxy-4,5-dimethyl-2(5H)-furanone (a) 10 g of 2-cyano-3-methyl-valero-γ-lactone [prepared as described in Chem. Abstr. 58, 5508 b (1962)] are treated, together with 14 g of borax in 150 ml of water, with 24.5 g of Caroat, 65 ml of 2 N sodium hydroxide being simultaneously added dropwise. After 30 minutes, the mixture is washed with 100 ml of ethyl acetate, acidified with 80 ml of 2 N sulphuric acid to pH 1 and extracted four times with 100 ml of ethyl acetate. The dried and concentrated extract gives 6.7 g (60%) of 2-cyano-2-hydroxy-3-methyl-valero-γ-lactone (epimer mixture) in the form of a yellow oil; n$_D^{20}$=1.4509.

IR: 3370 (OH); 2250 (weak, CN); 1782 (C=O).
MS: 155 (2%, M+), 128 (M-HCN), 133, 96, 83 (100%).

(b) 3.5 g of the foregoing lactone are refluxed with 2.75 g of sodium acetate for 3 hours in 50 ml of water. The cooled solution is extracted four times with 50 ml of acetic acid each time and the extract is dried over sodium sulphate and concentrated. There are obtained 1.43 g (50%) of gas-chromatographically pure 3-hydroxy-4,5-dimethyl-2(5H)-furanone.

NMR (CDCl$_3$): δ=7.2 ppm singlet broad/1 pr (OH); 4.91 quartet x quartet (J$_1$=6.5 Hz, J$_2$=1.5 Hz)/1 pr (H-5); 1.95 doublet (J=1.5 Hz)/3 pr (CH$_3$ at C-4); 1.44 doublet (J=6.5 Hz)/3 pr (CH$_3$ at C-5).

MS: 128 (M+), 113, 85, 83 (100%), 72, 57, 55.

EXAMPLE 3

Manufacture of 3-methylcyclopent-2-en-2-olone (a) A solution of 30.6 g of sodium ethylate in 400 ml of ethanol is treated with 80 g of diethylphosphonoacetonitrile. After 2 hours, 71.5 g of levulinic acid ethyl ester are added dropwise at 5° C. (which requires 60 minutes) and the turbid emulsion is then refluxed for 30 minutes. Subsequently, ca 300 ml of ethanol are distilled off and 400 ml of 1 N hydrochloric acid are added. The organic phase is separated, the aqueous phase is extracted three times with 200 ml of ether each time and the combined organic phases are concentrated. There are obtained 50.5 g (67%) of the cis-trans mixture of 5-cyano-4-methyl-4-pentenoic acid ethyl ester in the form of a clear yellowish liquid of boiling point 85°–86° C./0.05 Torr.

(b) 25 g of the foregoing ester are hydrogenated in the presence of 1 g of palladium/active carbon in 150 ml of methanol for 2 hours and the mixture is then filtered and the filtrate is concentrated. There are obtained 24.9 g (99%) of 2-methyl-adipomononitrile monoethyl ester of boiling point 76°–81° C./0.04 Torr.

IR: 2250 (CN), 1730 (C=O).

MS: 169 (M+), 154, 142, 129, 124 (M+-OEt, 100%), 101, 96, 88.

(c) 3.3 g of the ester obtained according to paragraph (b) are refluxed for 30 minutes together with 3.3 g of potassium tert.butylate, in 50 ml of toluene. The mixture is then treated with 50 ml of 1 N hydrochloric acid, the aqueous phase is separated and extracted three times with 40 ml of methylene chloride each time. The combined organic phases are dried over sodium sulphate, concentrated and distilled in a high vacuum and thus give 2.22 g (92%) of 2-cyano-3-methyl-cyclopentanone of boiling point 90° C./0.04 Torr.

IR: 2250 (CN); 1760 (C=O).

MS: 123 (M+, 100%), 108, 94, 80, 68, 55.

(d) 1.45 g of the nitrile obtained according to paragraph (c) are added, together with 2.3 g of borax and 0.96 g of sodium hydroxide, to 15 ml of water and the mixture is treated at 15° C. with 5.4 g of Caroat (Degussa) dissolved in 18 ml of water. After stirring for 45 minutes, the mixture is washed with 25 ml of ethyl acetate, acidified with 50 ml of 4 N sulphuric acid and extracted three times with 25 ml of ethyl acetate each time. The ethyl acetate phases are dried over sodium sulphate and concentrated to give 1.35 g (82%) of 2-cyano-2-hydroxy-3-methylcyclopentanone in the form of a brown oil; $n_D^{20} = 1.4708$; boiling point 120°-130° C./0.04 Torr.

IR: 3380 (OH), 2250 (weak, C≡N), 1760 and 1712 (C=O).

MS: 153 (M+), 135, 126, 83, 69.

(e) 1.5 g of the cyanohydrin obtained according to paragraph (d) are refluxed, together with 1.35 g of sodium acetate in 25 ml of water, for 5 hours. The cooled solution is extracted six times with 25 ml of ethyl acetate each time. The organic phases are combined, dried over sodium sulphate and concentrated to give 544 mg (45% yield) of 3-methylcyclopent-2-en-2-olone in the form of a yellow powder of melting point 92°-101° C.

EXAMPLE 4

Manufacture of 3,5-dimethylcyclopent-2-en-2-olone (a) 2.9 g (23.5 mmol) of 2-cyano-3-methyl-cyclopentanone [prepared as described in Example 3(c)] are dissolved in 60 ml of dry tetrahydrofuran and 2.8 ml of hexamethylphosphortriamide and the solution is treated with 0.62 g (25.9 mmol) of sodium hydride. 25.9 mmol of a 1.6 molar hexane solution of butyl lithium and subsequently 3.67 g (25.9 mmol) of methyl iodide are added under an argon atmosphere at −8° C. The mixture is held at ca 0° C. for a further 20 minutes (exothermic reaction) and then poured into 75 ml of 1 N hydrochloric acid and 100 g of ice. The aqueous phase is extracted three times with 50 ml of ether each time, dried over sodium sulphate and concentrated. The oil obtained is fractionally chromatographed on 140 g of silica gel with two parts of hexane and one part of ether. There are obtained 1.03 g (32%) of a diastereomeric mixture of 2-cyano-3,5-dimethylcyclopentanone in the form of a yellow oil.

IR: 2250 (CN), 1755 (C=O).

NMR (CDCl₃): δ = 1.6-3.5 ppm complex multiplet/5 pr (H-2, H-3, H-4, H-5); 1.29 and 1.14 in each case one doublet/6 pr (J=6 Hz, CH₃-3 and CH₃-5).

MS: 137 (M+), 122, 108, 94, 81, 68 (100%).

(b) 24 g (175 mmol) of the foregoing cyano compound are dissolved, together with 33.3 g (87.5 mmol) of borax and 14 g (350 mmol) of sodium hydroxide, in 300 ml of water and the solution is treated while cooling with 87 g (257 mmol) of Caroat in 266 ml of water. After stirring for a further 30 minutes, the pH of the solution is 5.6. The solution is acidified to pH 1 with 2 N sulphuric acid and extracted three times with 150 ml of ethyl acetate each time. The organic phases are dried over sodium sulphate and concentrated to give 26.2 g (98%) of 2-cyano-2-hydroxy-3,5-dimethylcyclopentanone in the form of a colourless viscous oil. This oil can be distilled at 50°-60° C./0.035 Torr; $n_D^{20} = 1.4577$.

IR: 3450 (strong, OH), 2250 (weak, CN), 1760 (strong, C=O).

NMR (CDCl₃): δ = 4.4 ppm, singlet broad/1 pr (OH); 3.1-1.6 multiplet/4 pr (H-3, H-4, H-5); 1.5-1.0 multiplet/6 pr (CH₃-3 and CH₃-5).

MS: 153 (M+), 135, 126, 120, 109, 96, 83 (100%), 74.

(c) 23.2 g (152 mmol) of the foregoing cyanohydrin are refluxed for 40 minutes with 18.6 g (227 mmol) of sodium acetate in 380 ml of water while passing in a vigorous nitrogen stream. The cooled solution is extracted three times with 150 ml of methylene chloride each time and the combined extracts are dried over sodium sulphate and concentrated. There are obtained 12.0 g (63%) of 3,5-dimethylcyclopent-2-en-2-olone of melting point 92°-95° C. (from ether/hexane).

IR (CHCl₃): 3530 and 3350 (OH), 1710 and 1660 (strong, C=O).

MS: 126 (M+, 100%), 111, 98, 97, 83, 69, 56.

EXAMPLE 5

Manufacture of 3,5-dimethylcyclopent-2-en-2-olone (a) 29.5 g (77.5 mmol) of borax and 24.8 g (0.62 mol) of sodium hydroxide are dissolved in 310 ml of water and treated while cooling (17° C.) with 65 g (310 mmol) of 3-carboethoxy-2-cyano-3,5-dimethylcyclopentanone (prepared from ethyl methacrylate and sodium cyanide according to H. Stetter et al, Liebig's Annalen d. Chem. 1979, 944-949). 132.2 g (403 mmol) of Caroat dissolved in 428 ml of water are added dropwise at 13° C. to 19° C. within 25 minutes and the mixture is stirred at room temperature for 3 hours. For the working-up, the mixture is acidified with 30 ml of sulphuric acid (2:1) and extracted four times with ethyl acetate. The organic phase is dried over sodium sulphate, concentrated and dried in a high vacuum for 2 hours. There are obtained 69.8 g (100%) of 3-carboethoxy-2-cyano-2-hydroxy-3,5-dimethylcyclopentanone in the form of a diastereomeric mixture; $n_D^{20} = 1.4658$.

IR: 3400 (OH); 2270 (weak, CN); 1720 (broad, C=O).

NMR (CDCl₃): δ = 4.5-3.9 ppm multiplet/2 pr (ester CH₂); 3-1.7 complex multiplet/4 pr (3 ring protons+OH); 1.7-1.0 multiplet/9 pr (3×CH₃).

MS: 225 (M+), 198, 180.

(b) 66.3 g (0.03 mol) of the foregoing 3-carboethoxy-2-cyano-2-hydroxy-3,5-dimethylcyclopentanone and 30.2 g (0.4 mol) of anhydrous sodium acetate are treated with 350 ml of water. The mixture is refluxed for 6 hours. For the working-up, the mixture is adjusted to pH 7 with saturated sodium hydrogen carbonate solution and then extracted four times with methylene chloride. The organic phases are dried over sodium sulphate, concentrated and dried in a high vacuum for 1 hour. (The product can, however, also be directly crystallised from the reaction mixture). There are obtained 42.6 g (73%) of crystalline 2-carboethoxy-2,4-dimethylcyclopent-4-en-5-olone of melting point 92°-93° C.

IR (CHCl₃): 3540 and 3360 (OH); 1725 (COOC₂H₅); 1670 (C=O).

NMR (CDCl₃): δ=6.1 ppm singlet broad/1 pr (OH); 4.14 quartet (J=7.4 Hz)/2 pr (O—CH₂—Me); 2.95 doublet×quartet (J₁=17.6 Hz, J₂=1 Hz)/1 pr and 2.22 doublet×quartet (J₁=17.6 Hz, J₂=1 Hz)/1 pr (CH₂ at C-3); 2.01 doublet×doublet (J₁=J₂=1 Hz)/3 pr (CH₃ at C-4); 1.39 singlet/3 pr (CH₃ at C-2); 1.20 triplet (J=7.4 Hz)/3 pr (CH₃ of the ethyl ester).

MS: 198 (M+), 180, 153, 141, 134, 124 (100%).

(c) 4.8 g (24 mmol) of the foregoing 2-carboethoxy-2,4-dimethylcyclopent-4-en-5-olone are treated with 48 ml of 2N sodium hydroxide solution and the mixture is stirred at room temperature for 1.5 hours. For the working-up, the mixture is adjusted to pH 3 with 10% sulphuric acid and extracted three times with ethyl acetate. The combined organic phases are dried over sodium sulphate, concentrated and dried in a high vacuum for 2 hours. There are obtained 3 g (58.5%) of 2-carboxy-2,4-dimethylcyclopent-4-en-5-olone of melting point 98°–105° C., with elimination of carbon dioxide.

IR (KBr): 3270 (broad, COOH); 1712 and 1690 (C=O); 1620 (C=C).

NMR (CD₃OD): δ=5.9 ppm singlet broad (DOH); 2.92 doublet x quartet (J₁=17.2 Hz, J₂=1 Hz)/1 pr and 2.25 doublet x quartet (J₁=17.2 Hz: J₂=1 Hz)/1 pr (CH₂ at C-3); 1.97 doublet x doublet (J₁=J₂=1 Hz)/3 pr (CH₃ at C-4); 1.30 singlet/3 pr (CH₃ at C-2). MS: 170 (M+), 152, 134, 126, 124 (100%), 111.

(d) 85.1 g (0.5 mol) of the acid obtained according to paragraph (c), namely 2-carboxy-2,4-dimethylcyclopent-4-en-5-olone, are treated with 851 ml of 10% sulphuric acid and the mixture is refluxed for 45 minutes. For the working-up, the mixture is adjusted to pH 7 with 2N sodium hydroxide solution and then extracted three times with methylene chloride. The combined organic phases are dried over sodium sulphate and dried in a high vacuum for 1 hour. There are obtained 57.4 g (91%) of crystalline 3,5-dimethylcyclopent-2-en-2-olone of melting point 93°-94° C. The product is identical with the product obtained according to paragraph (c) of Example 4.

EXAMPLE 6

The same product as that of paragraph (d) of Example 5 is obtained in 90% yield when the 2-carboethoxy-2,4-dimethylcyclopent-4-en-5-olone [see paragraph (b) of Example 5] is treated directly under the foregoing conditions; the product melting at 93°–94° C.

EXAMPLE 7

The same product as that of paragraph (d) of Example 5 can also be obtained by treating 3-carboethoxy-2-cyano-3,5-dimethylcyclopentanone [see paragraph (a) of Example 5] with Caroat, acidifying the resulting mixture of pH 1 and then refluxing the mixture for 24 hours. Working-up as described in paragraph (d) of Example 5 yields 70% of pure crystalline 3,5-dimethylcyclopent-2-en-5-olone of melting point 92°–93° C. (from water).

EXAMPLE 8

Manufacture of 3,5-diethylcyclopent-2-en-2-olone (a) 3-Carboethoxy-2-cyano-3,5-diethylcyclopentanone is obtained according to H. Stetter et al, Liebig's Annalen d. Chem. 1979, 944, in 80% yield when ethyl 2-ethylacrylate is used in place of ethyl methacrylate.

The 3-carboethoxy-2-cyano-3,5-diethylcyclopentanone boils at 95°–116° C./10.05 Torr.

IR: 2260 and 2210 (CN), 1755 (C=O), 1728 (COOEt).

NMR (CDCl₃): δ=4.26 ppm quartet/2 pr (ester CH₂), 4.0-3.1 various singlets of the diastereomers/1 pr (H at C₂); 2.8-1.3 multiplet/7 pr (3 remaining ring protons and 2 ethyl CH₂); 1.3 triplet/3 pr (ester CH₃); 0.95 triplet/6 pr (2 ethyl CH₃).

MS: 237 (M+), 208, 192, 180, 163, 152, 142, 135 (100%), 126, 106.

This nitrile is oxidised with Caroat and work-up in a manner analogous to that described in paragraph (a) of Example 5, there being obtained in quantitative yield 3-carboethoxy-2-cyano-2-hydroxy-3,5-diethylcyclopentanone; $n_{20}{}^D=1.4502$.

IR: 3350 (OH), 2250 (weak, CN), 170 (broad, ketone+ester).

MS: 253 (M+), 237, 226, 208, 181, 152 (100%), 141, 129, 124, 109.

(b) The cyanohydrin obtained according to paragraph (a) is refluxed in aqueous solution and worked-up according to the procedure described in paragrah (b) of Example 5. 2-Carboethoxy-2,4-diethyl-cyclopent-4-en-5-olone is obtained in 80% yield.

IR: 3360 (OH), 1725 (COOC₂H₅), 1705 (C=O), 1655 (C=C).

NMR (CDCl₃): δ=6.0 ppm, singlet, broad/1 pr (OH); 4.18 quartet/2 pr (ester CH₂); 2.95 doublet/1 pr and 2.35 doublet/1 pr (CH₂ at C-3); 2.7 to 1.5 multiplet/4 pr (2×CH₂ at ethyl); 1.4 to 0.7 multiplet/9 pr (3×CH₃).

MS: 226 (M+), 197, 181, 162, 152 (100%), 137, 124, 109.

(c) By treating the foregoing ester with sodium hydroxide in a manner analogous to that described in paragraph (c) of Example 5 there is obtained crystalline 2-carboxy-2,4-diethylcyclopent-4-en-5-olone in 71% yield.

IR: 3520 (OH), 3200 (broad, COOH), 1705 (broad, C=O ketone, ester) 1655 (C=C).

NMR (CDCl₃): δ=7.9 ppm singlet/2 pr (OH, COOH); 3.06 doublet/1 pr and 2.4 doublet/1 pr (CH₂ at C-3); 2.8 to 1.5 multiplet/4 pr (2×CH₂ at ethyl); 1.17 triplet/3 pr and 0.9 triplet/3 pr (2×CH₃).

MS: 169, 154, 126 (100%), 111, 108.

The foregoing acid decomposes upon warming or standing to give 3,5-diethylcyclopent-2-en-2-olone of melting point. 38.5°–39° C.

We claim:

1. A process for the manufacture of α-hydroxycarbonyl compounds of the formula:

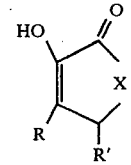

wherein:
R represents methyl or ethyl;
R' represents hydrogen, methyl or ethyl; and
X represents oxygen, >CH₂, >CHCH₃ or >CHCH₂CH₃;
which comprises oxidizing a compound of the formula:

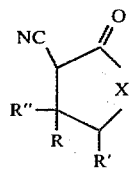

wherein:
R" represents hydrogen when X is oxygen and represents —COOR''' or hydrogen when X is not oxygen; and
R''' represents hydrogen or an alkyl group of from one to six carbons; with a caroate to provide a cyanohydrin of the formula

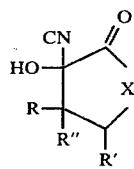

and subjecting said cyanohydrin II to a cyanohydrin cleavage and, when R" is —COOR''', cleaving off the —COOR''' group.

2. The process of claim 1 wherein the cyanohydrin

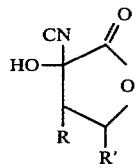

is prepared by oxidizing a compound of the formula:

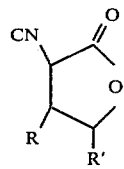

3. The process of claim 2 wherein R and R' are methyl.

4. The process of claim 1 wherein the cyanohydrin

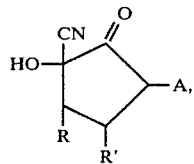

(wherein A is hydrogen, methyl or ethyl) is prepared by oxidizing a compound of the formula

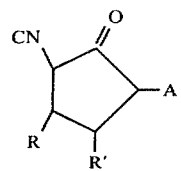

5. The process of claim 4 wherein R and 4' are methyl.

6. The process of claim 4 wherein R is methyl and R' is hydrogen.

7. The process of claim 5 or 6 wherein A is hydrogen.

8. The process of claims 5 or 6 wherein A is methyl.

9. The process of claim 1 wherein the cyanohydrin

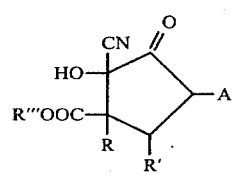

(wherein A is hydrogen, methyl or ethyl) is prepared by oxidizing a compound of the formula:

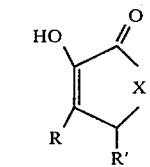

10. The process of claim 9 wherein R and R' are methyl.

11. The process of claim 9 wherein R is methyl and R' is hydrogen.

12. The process of claim 10 or 11 wherein A is hydrogen.

13. The process of claim 10 or 11 wherein A is methyl.

14. The process according to claim 9 wherein R is methyl, R' is hydrogen, R''' is ethyl and A is methyl.

15. The process according to claim 9 wherein R is ethyl, R' is hydrogen, R''' is ethyl, and A is ethyl.

16. A process for the manufacture of α-hydroxycarbonyl compounds of the formula $$\text{(structure I)}$$

wherein:
R represents methyl or ethyl;
R' represents hydrogen, methyl or ethyl; and
X represents oxygen, >CH$_2$, >CHCH$_3$ or >CHCH$_2$CH$_3$;
which comprises subjecting a cyanohydrin of the formula:

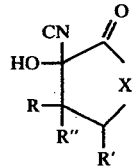

II wherein:

R" represents hydrogen when X is oxygen and represents —COOR''' or hydrogen when X is not oxygen, and R''' represents hydrogen or an alkyl group of from one to six carbons; to a cyanohydrin cleavage and, when R" is —COOR''' cleaving off the —COOR''' group.

17. The process of claim 16 wherein the cyanohydrin is

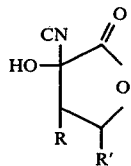

18. The process of claim 17 wherein R and R' are methyl.

19. The process of claim 16 wherein the cyanohydrin is

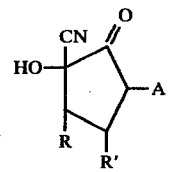

20. The process of claim 19 wherein R and R' are methyl.

21. The process of claim 19 wherein R is methyl and R' is hydrogen.

22. The process of claim 20 or 21 wherein A is hydrogen.

23. The process of claims 20 or 21 wherein A is methyl.

24. The process of claim 16 wherein the cyanohydrin is

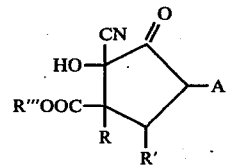

wherein A is hydrogen, methyl or ethyl

25. The process of claim 24 wherein R and R' are methyl.

26. The process of claim 24 wherein R is methyl and R' is hydrogen.

27. The process of claim 25 or 26 wherein A is hydrogen.

28. The process of claim 25 or 26 wherein A is methyl.

29. The process according to claim 24 wherein R is methyl, R' is hydrogen, R''' is ethyl and A is methyl.

30. The process according to claim 24 wherein R is ethyl R' is hydrogen, R''' is ethyl, and A is ethyl.

* * * * *